United States Patent [19]

Kraus

[11] Plant 4,275

[45] Jul. 4, 1978

[54] AZALEA PLANT-LUCILLE K

[76] Inventor: Fred Kraus, 19250 Hesperian Blvd., Hayward, Calif. 94541

[21] Appl. No.: 825,954

[22] Filed: Aug. 19, 1977

[51] Int. Cl.[2] ..... A01H 5/00

[52] U.S. Cl. ..... Plt./55

[58] Field of Search ..... Plt./55

*Primary Examiner*—Robert E. Bagwill
*Assistant Examiner*—James R. Feyrer
*Attorney, Agent, or Firm*—James R. Cypher

[57] ABSTRACT

This invention relates to a new and distinct variety of Belgian-Indica type Azalea named Lucille K which is a sport of Azalea U.S. Plant Pat. No. 1,159 named Red Wing.

Lucille K is like its parent Red Wing in many of its vegetative characteristics, but is distinctly different from Red Wing in the following ways: Flower color, flower petal always has a pronounced white margin, the flowers are hardier resulting in longer blooming, and the plant flowers naturally on or about Valentine's Day (February 14th).

2 Drawing Figures

BACKGROUND OF THE INVENTION

The present sport was discovered by me in my commercial nursery in Hayward, Calif., where I was growing beds of Red Wing under greenhouse conditions for the 1973 Christmas season. The new variety did not bloom in December 1973, as did all the other Red Wings in the beds; but instead bloomed around Valentine's Day, Feb. 14, 1974.

When the plant came into bloom it was distinctly different from Red Wing in its flower color with silvery-white petal margining and more hardy blossoms.

It was, therefore, taken for propagation by cuttings. Five hundred repeated vegetations and flowerings of the sport by me through asexual reproduction from February 1974 through 1976 under normal environment conditions in a greenhouse at my commercial nursery in Hayward, Calif., show that the new and distinct characteristics of the sport come true to form and are established and transmitted through succeeding propagations.

BRIEF SUMMARY

The new sport "Lucille K" has the same vegetative characteristics as its parent Red Wing except for the following distinct differences:

1. Lucille K's basic flower color is Rose Madder (HCC 23). The throat spots of the corolla tube are Chrysanthemum Crimson (HCC 824/1). Red Wing's flowers are basically red with an undertone of orange. On outdoor grown Red Wing plants this produces a rose shade (1-J-4 through 1-J-6) with the outside of the outer trumpet sometimes showing tracings of white and the upper part of the throat overlaid with maroon (4-L-6). On greenhouse grown Red Wing plants, the flowers are deeper shade (3-J-6) with the upper part of the throat overlaid with a deeper maroon.

2. The flower petals always have a pronounced silvery-white margin which is strongly crenulate whereas Red Wing has no white margin.

3. The flower petals are a heavier, hardier substance than the petals of Red Wing and more waxen in texture.

4. Individual blooms last 10 to 12 days as opposed to the blooms of Red Wing which last about 2 to 3 days.

5. The flowers are more resistant than Red Wing to shattering and falling-off the plant when being transported commercially.

6. Once in bloom, the plant will have blooms on it for about 1 month, whereas Red Wing will be done blooming in about 1 week.

7. When grown in greenhouses it reliably flowers around Valentine's Day (February 14) without employing any special techniques, whereas Red Wing naturally flowers in December.

The new sport is a good hardy greenhouse plant of exceptional beauty and distinct color with pronounced white petal margining and can be easily forced to bloom any month of the year desired, but naturally blooms in February.

DESCRIPTION OF THE PHOTOGRAPH

This new variety of Azalea plant named Lucille K is illustrated by the accompanying photographs which show the form and color characteristics of the plant and its bloom and foliage; the color rendition being as nearly true as is reasonably possible to obtain by conventional photographic procedures.

Photograph 1 shows the entire plant and Photograph 2 shows a close up view of the flowers.

DETAILED DESCRIPTION

Referring to the botanical details of this new variety, the following is an outline description. All plants were grown under normal environmental conditions in greenhouses and all color readings were taken in the greenhouse during daylight hours. All colors are based on the Royal Horticultural Society Color Chart.

Since the sport is like its parent Red Wing in many vegetative characteristics, I will describe only those characteristics that differ from Red Wing.

PLANT

Blooming season: Naturally blooms for Valentine's Day (February 14th) but can be easily forced to bloom any month of the year by employing special techniques.

FLOWER

Permanence: Long lasting remaining in bloom about 1 month with individual flowers lasting 10 to 12 days with no fading or change of color as flowers age.

Color: Basic flower color is Rose Madder (HCC 23) with a pronounced silvery-white petal margining which is strongly crenulate. The throat spots of the corolla tube are Chrysanthemum Crimson (HCC 824/1).

PETALS

Texture: Very heavy, very waxen.

Appearance: Velvety, inside and out with edges strongly crenulate.

Persistence: Petals do not shatter or drop off the plant when transported under commercial conditions.

I claim:

1. A new and distinct variety of Azalea of the Belgium Indica type as described and illustrated, known by the cultivar name Lucille K.

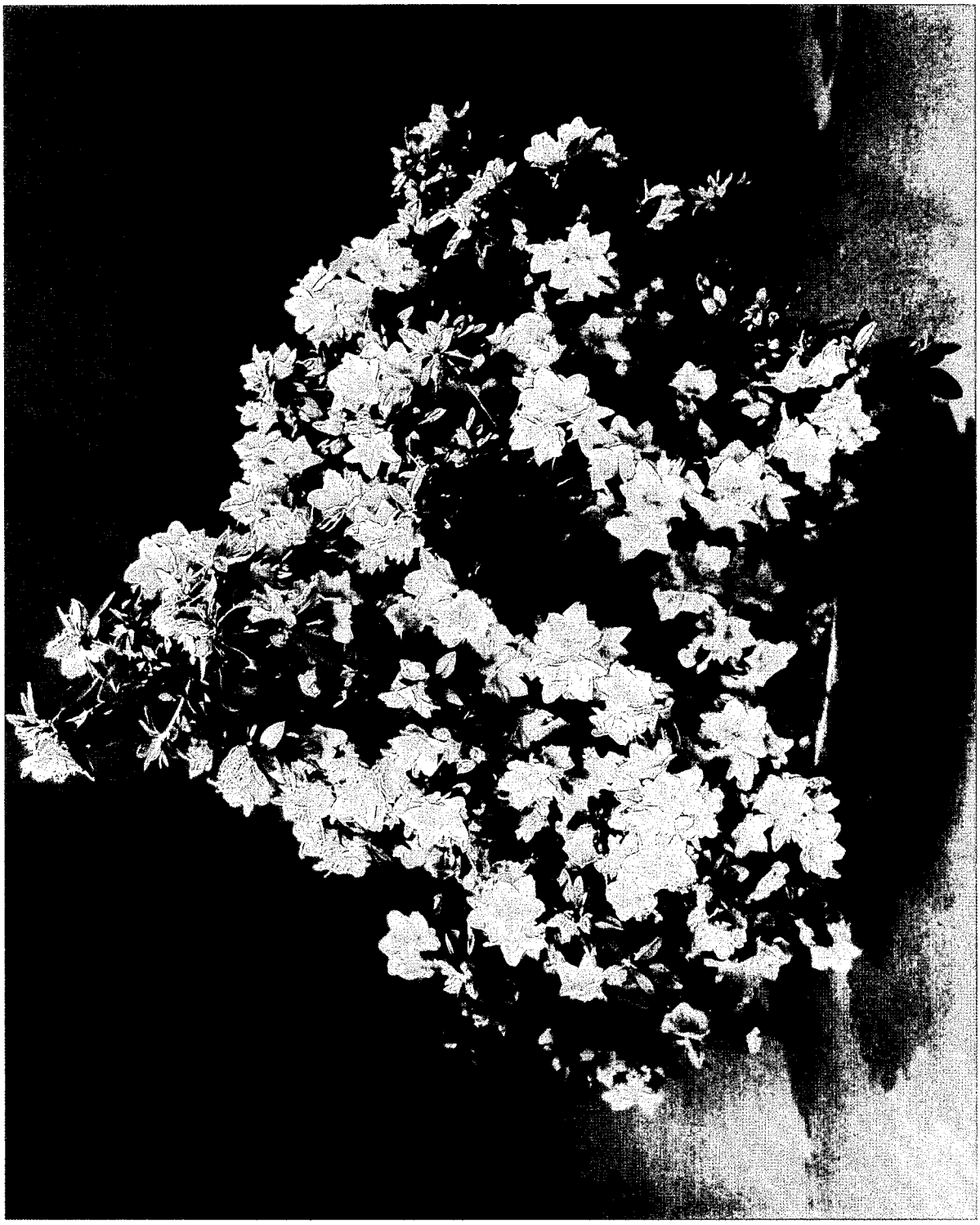

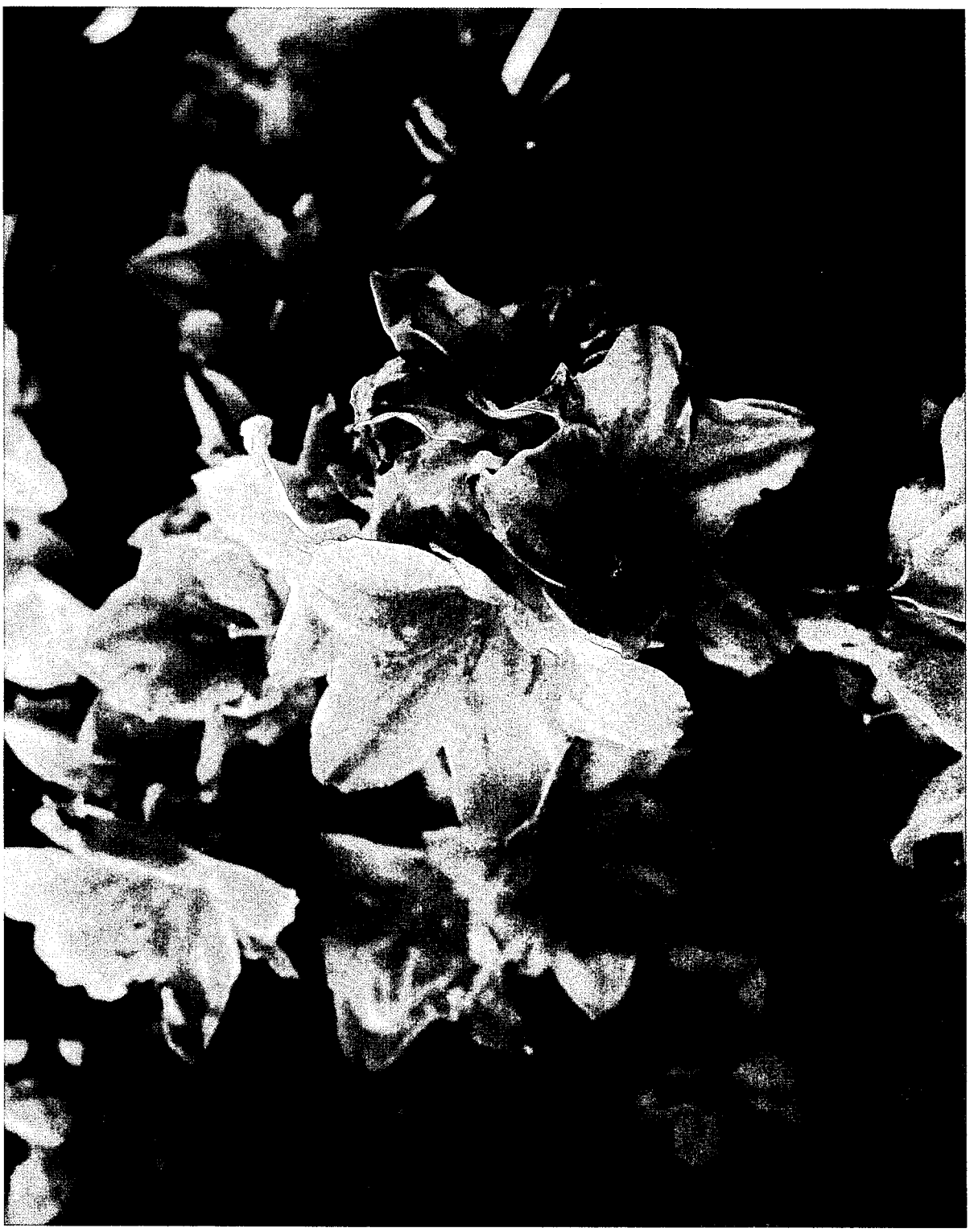

* * * * *